United States Patent [19]

Kuntz

[11] 4,349,921
[45] Sep. 21, 1982

[54] INTERVERTEBRAL DISC PROSTHESIS

[76] Inventor: J. David Kuntz, 899 Lahakas Blvd., Kitimat, B.C., Canada

[21] Appl. No.: 159,843

[22] Filed: Jun. 16, 1980

[51] Int. Cl.³ ............................................. A61F 1/00
[52] U.S. Cl. ........................................................... 3/1
[58] Field of Search ................... 3/1, 1.9, 1.91, 1.911, 3/1.912, 1.913; 128/92 C, 92 CA, 92 R, 92 EC

[56] References Cited

U.S. PATENT DOCUMENTS

| | | | |
|---|---|---|---|
| 2,677,369 | 5/1954 | Knowles | 128/92 R |
| 3,685,058 | 8/1972 | Tronzo | 128/92 EC X |
| 3,867,728 | 2/1975 | Stubstad et al. | 3/1.91 |
| 3,875,595 | 4/1975 | Froning | 3/1 |
| 4,040,131 | 8/1977 | Gristina | 3/1.91 |
| 4,245,359 | 1/1981 | Stuhmer | 3/1.9 |
| 4,257,129 | 3/1981 | Volz | 3/1.911 |

FOREIGN PATENT DOCUMENTS

| | | | |
|---|---|---|---|
| 2263842 | 7/1974 | Fed. Rep. of Germany | 3/1.91 |
| 2804936 | 8/1979 | Fed. Rep. of Germany | 3/1.91 |
| 2372622 | 6/1978 | France | 3/1.9 |

Primary Examiner—Clifford D. Crowder

[57] ABSTRACT

An intervertebral disc prosthesis intended to replace a natural intervertebral disc and to restore the normal intervertebral spacing without complete loss of flexibility of the spinal joint. The prosthesis comprises a body of biologically-acceptable material suitably dimensioned and shaped to replace a natural disc. One of the longitudinal ends of the prosthesis has suitable means, e.g. a raised flange, to facilitate handling of the prosthesis and to prevent penetration to an excessive depth into the spinal joint. The other longitudinal end is preferably wedge-shaped to facilitate insertion into the intervertebral space. The superior and inferior surfaces are preferably provided with surface characteristics to produce a "friction-fit" and are convex to correspond to the adjacent vertebral surface. The prosthesis is inexpensive to manufacture and can be implanted quite easily with little danger to the patient. Moreover, the prosthesis maintains at least some of the flexibility of the joint while remaining firmly anchored in place.

52 Claims, 15 Drawing Figures

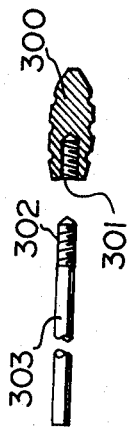
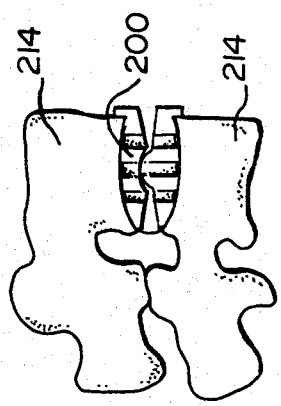
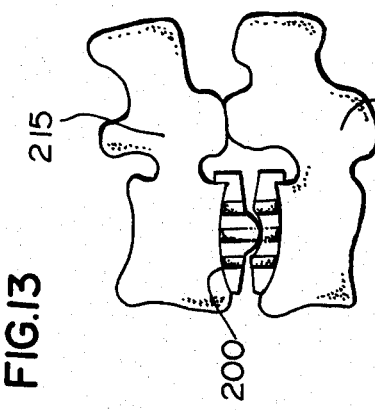
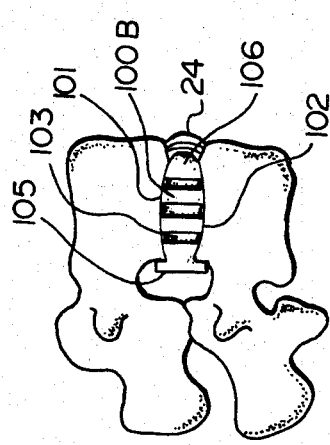
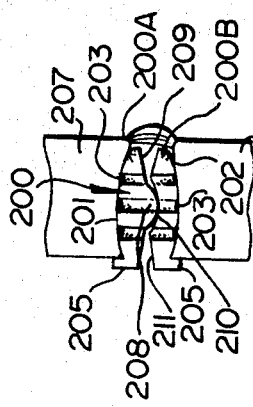

INTERVERTEBRAL DISC PROSTHESIS

BACKGROUND OF THE INVENTION

1. Field of the Invention

This invention relates to an intervertebral disc prosthesis and to surgical techniques for implanting the prosthesis.

The vertebrae of the spinal column are connected together by intervertebral fibrocartilaginous discs. The discs maintain a separation between the vertebrae, but occasionally become narrowed so that the intervertebral separation is reduced. This reduction in separation has a number of painful and unpleasant consequences, for example, in the cervical region of the spine, it can result in cervical spondylosis, vertebral artery syndrome and painful arc syndromes. These symptoms are described in more detail below.

1. Description of the Prior Art

Procedures have been developed in the prior art for alleviating the symptoms resulting from intervertebral disc failure.

One such procedure involves fusing the adjacent vertebrae by removing the damaged disc and inserting a plug or wedge of bone removed from another part of the patient's skeleton.

An example (known as the "Cloward technique") of such a procedure for the cervical vertebrae is described in "ORTHOPAEDICS—PRINCIPLES AND THEIR APPLICATION," Samuel L. Turek, M.D., Lippincott Company, Third Edition, pp. 761-763, in which a hole is drilled in the spinal column straddling the damaged disc space and including parts of the adjacent vertebrae. The hole is then filled with a cylindrical plug or dowel of bone in order to fuse the vertebrae together.

Fusion of vertebrae together necessarily results in complete loss of flexibility of the spinal column at this location and is thus disadvantageous. Accordingly, proposals have been made in the past to replace the damaged or diseased disc with a disc prosthesis intended to duplicate the function of the natural disc to some extent.

French patent application publication No. 2,372,622, of Bernard Fassio, published June 30, 1978, discloses one such disc prosthesis. This consists of a flat circular plate having central hemispherical projections on each face thereof. The hemispheres allow articulation of the joint while the flat plate maintains separation. It is believed, however, that such a prosthesis would not be entirely satisfactory because the hemispheres would not correspond closely to the shape of the adjacent vertebral surfaces. This could result in crushing of the cancellous vertebral bone by the hemispheres and consequent reduction in separation and articulation of the joint.

Another disc prosthesis is disclosed in U.S. Pat. No. 3,867,728 of Stubstad et al., issued Feb. 25, 1975, assigned to Cutter Laboratories Inc. The prosthesis is a flattened kidney shaped block of elastomeric synthetic resin. The shape of the prosthesis is intended to conform closely to the space in a spinal disc from which the necleus pulposus has been removed. One disadvantage of this type of prosthesis is that elastomeric materials have been known to disintegrate in the body and to break down under repeated stressing over prolonged periods. Moreover, it is disclosed that the surface of the prosthesis may be porous to allow tissue ingrowth, but a porous surface is more prone to harbor bacteria due to the large surface area involved. In a porous surface in which tissue ingrowth has occurred, there is also increased possibility of repeated injury at the interface between the bone and prosthesis due to tearing of fibrous tissue or prosthetic fibers with subsequent tissue reaction including foreign body rejection.

A major disadvantage of a porous material is that if there is actual tissue ingrowth into the prosthesis, removal could be difficult. Curetting out the prosthesis would lead to hemorrhage of a very vascular surface area, caused by the tissue ingrowth, with subsequent increased danger of cord compression secondary to hemorrhage.

Besides, any porous material allowing tissue ingrowth for stability in a cervical spine would be dangerous as the esophagus, which lies anteriorly, could become adhered to the prosthesis with resultant dysphagia or difficulty in swallowing.

There is consequently a need for a prosthesis that remains stably in place when implanted but does not have the difficulties referred to above associated with porous surfaces.

West German Offenlegungsschrift No. 2,263,842 in the name of Hoffmann-Daimler, published on July 4, 1974 discloses yet another type of disc prosthesis. In its simplest form, this prosthesis consists of a circular disc having smooth convex faces. The disc may be made of a synthetic material. This simple form, however, may become displaced when implanted and could possibly damage the neural canal.

The known prostheses are often made of different materials bonded together to allow movement within the prosthesis, but this weakens the overall loading strength of the prosthesis. This is particularly the case when the prosthesis is submitted to repeated stresses. Bonded materials can become fatigued under stress and, due to the very thin spaces involved, any multiple layered prosthesis would involve quite thin layers of material. This would increase the problem of breakage and migration of fragments which could have hazardous consequences in the spinal area.

It is believed that each of the prostheses referred to above is intended only for the lumbar area of the spine. For example, the Stubstad et al. patent describes insertion through an anterior approach which is, in fact, a 'retroperitoneal' approach. There is therefore a need for a disc prosthesis that can be used in the cervical area of the spine as well as just the lumbar area.

Another difficulty of the known prostheses is the difficulty of handling them during surgical implantation. In particular, difficulty is often encountered in removing the prostheses once implanted should adjustment or replacement be required.

SUMMARY OF THE INVENTION

It is an object of the present invention to provide an improved intervertebral disc prosthesis.

According to one aspect of the invention there is provided an intervertebral disc prosthesis, comprising a body of biologically compatible material having a superior surface, an inferior surface and opposed anterior and posterior ends, and means located at one of said opposed ends for facilitating holding of the prosthesis during its insertion into or removal from an intervertebral disc space.

The prosthesis is designed to restore the normal width of the disc space. The superior surface of the disc space is usually slightly convex. This corresponds to the slight concavity in the inferior surface of the vertebral body. The inferior side of the disc space is usually more nearly planar corresponding to the superior surface of the vertebral body, though it too is often slightly convex. Accordingly, either both main surfaces of the disc prosthesis may be made slightly convex, or one may be slightly convex and the other planar. Although it is not preferred, both surfaces may be planar if desired.

Replacement of the defective discs with a disc prosthesis as defined above restores the intervertebral disc space and thus immediately corrects many of the problems producing painful or unpleasant symptoms.

BRIEF DESCRIPTION OF THE DRAWINGS

FIG. 11 is a simplified lateral representation of a prosthesis implanted according to the steps shown in FIGS. 5 to 10;

FIG. 12 is a simplified lateral view of a prosthesis according to a third embodiment of the invention implanted in an intervertebral space;

FIG. 13 is a view similar to FIG. 12 showing the prosthesis located in the cervical region of the spine; and FIG. 14 is a view similar to FIG. 12 showing the prosthesis located in the lumbar region of the spine;

FIG. 15 is a cross-sectional view of yet another embodiment of this invention showing an alternative means for holding the prosthesis.

Figure 6:
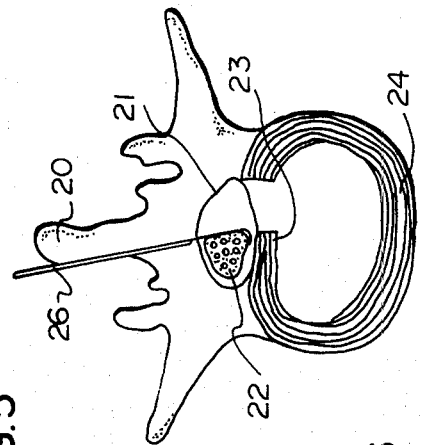
FIGS. 5 to 10 are simplified plan views of an intervertebral disc space showing the steps in the method of inserting a prosthesis according to a second embodiment of this invention.

As the first step towards putting the present invention into practice is for the physician to recognize the symptoms which suggest prosthetic disc replacement, and since these symptoms are not generally well known in the case of the cervical region of the spine, they are briefly discussed in the following.

Symptoms Suggesting Prosthetic Disc Replacement

(I) Cervical Disc Disease (Cervical Spondylosis)

This is a clinical syndrome consisting of neck pain and stiffness and crepitation on neck movement, with associated posterior occipital and frontal headaches. There are also radicular pains towards the shoulders and arms associated with numbness and weakness in the arms and hands. It is characterized by restricted range of movement of the neck especially in extension, and often is associated with hypoactive reflexes in the affected arm and decreased sensation in the particular dermatome distribution of the involved nerve root.

The radiological findings are characteristically narrowing of the disc space, narrowing of the outlet foramen at the involved level, and osteophytes and proliferative bony changes noted on the vertebral bodies and the joints of Luschka.

Replacement of the cervical discs with disc prostheses is designed to restore the width of the intervertebral disc space. This in turn restores the superior-inferior diameter or height of the outlet foramen which has been diminished with the narrowing of the disc space. It also restores the anatomy of the apophyseal joint surfaces posteriorly to a more normal anatomical relationship to each other. By opening the foramen the compression of the nerve root passing through the narrow foramen is subsequently relieved. This in turn leads to relief of the symptoms of headache, neck pain, pain radiating to the shoulders and arms and associated weakness and numbness in the arms and hands.

(B) Vertebral Artery Syndrome

It is noted that the vertebral artery courses through the neck carried in the foramen transversarium of the transverse processes of the vertebrae. With narrowing of the disc space it is noted that the space between the adjacent transverse process is also narrowed and this leads to subsequent kinking outward of the accompanying vertebral artery in these spaces between the adjacent foramina through which it passes. This leads to impaired flow within the vessel and this is accentuated at various positions of the neck leading to the clinical syndrome of dizziness, blackouts, momentary blurred vision, occasional tinnitus related to imparied vertebral artery flow. The latter two components of this syndrome may be related to imparied vertebral artery blood flow of the nuclei of the involved cranial nerves in the midbrain. With regard to the blurred vision the impaired flow to the occipital area of the brain involved in vision could also be a factor.

It has been noted that in restoring the width of the vertebral disc space with the use of a cervical disc prosthesis or intervertebral disc spacer results in obliteration of these associated vertebral artery syndrome complaints of dizziness, blackouts, intermittent blurred vision and tinnitus. It is noted that in using the intervertebral disc prosthesis the distance between the transverse processes is also restored and hence the kink in the vertebral artery is straightened out as the vessel is now drawn out to its normal length. Hence the turbulent flow situation is restored to a laminar type flow through the vessel with subsequent disappearance of the intermittent vertebral artery symptoms related to intermittent impaired flow through the vessel with various positions of the neck.

(C) Painful Arc Syndromes

It is noted that nerve root compression in the outlet foramen of the cervical spine leads to muscle paralysis and weakness distally in the arm in the particular myotomes supplied by the particular nerve root involved. This may result in syndromes of painful shoulder due to muscle imbalance of the muscle groups crossing the shoulder joint. If a particular muscle is paralyzed, the antagonistic muscle will suddenly work unopposed, creating a muscle imbalance situation in the shoulder joint with subsequent creation of painful shoulder syndrome. For instance, in a C4–5 disc degeneration with narrowing, the C5 nerve root may be obstructed in the outlet foramen. In a C5–6 disc degeneration, the narrowing and obstruction of the outlet foramen may involve the C6 nerve root.

Since these particular roots supply supraspinatus muscle, which tends to hold the humeral head tightly into the glenoid on shoulder abduction movements, the head is not held tightly into the socket when paresis of this muscle occurs. In addition, the biceps muscle which is also supplied by C5 and C6 nerve roots may also be weakened. Since the long head of the biceps tendon passes over the humeral head to the supraglenoid tubercle, its function in holding the humeral head depressed in the socket is subsequently lost. It normally acts as a downward force on the humeral head.

In constrast, the force of the long head of the triceps muscle, an antagonistic muscle, comes into play. Since it arises from the infraglenoid tubercle and passes across the elbow, it acts as a force tending to drive the humeral head upward toward the acromion. Since triceps is supplied by the C7 and C8 nerve roots, its function continues unimpaired when the disc degeneration involves only the roots of the higher levels as described. This leads to a muscle imbalance situation in which the humeral head may ride up superiorly in the glenoid socket. This causes subsequent contact between the supraspinatus tendon and greater tuberosity under the acromion as the arm is abducted. This can lead to the following:
(1) Sub-acromial bursitis
(2) Painful arc syndrome
(3) Rotator cuff degeneration
(4) Frozen shoulder or adhesive capsulitis
(5) Shoulder-hand syndrome.

It is noted that in the above list, rotator cuff degeneration is mentioned. It is theorized that this could be created in the following manner: If the humeral head is riding high in the socket, the supraspinatus tendon insertion is interposed between the two bony surfaces of head of humerus and the acromion. It is known that there is a very delicate capillary anastomosis in the distal half inch of the supraspinatus tendon created by vessels passing through the substance of the tendon from the muscle proximally and the greater tuberosity distally. This anasatomosis occurs within the distal half inch of the supraspinatus tendon where it inserts into the greater tuberosity of the humerus.

When the above muscle imbalances occurs, the humeral head rides higher in the socket with subsequent pressure between head of humerus and the overlying acromion, local pressure on the interposed tendon would shut off this delicate capillary anastomosis causing local necrosis of the interposed tissue. This is analogous to pressure necrosis of skin as seen in decubitis ulcers.

The ischemia of the supraspinatus tendon may lead to collagen degeneration, deposition of calcium salt in these tissues as seen in dystrophic calcification, calcific tendinitis, and actual supraspinatus tendon rupture secondary to the muscle pull through degenerate tendon.

Restoration of the diameter of the outlet foramen allows a return of nerve function to the muscles about the shoulder girdle. This leads to correction of the muscle imbalance situation with restoration of the normal tone to the muscles which determine the position of the humeral head in the socket. This can be readily accomplished through the use of the prosthetic cervical disc spacer as described. With return of normal muscle tone through post-operative shoulder physiotherapy, the muscle bulk is restored, muscle balance is restored and subsequently the painful arc syndrome can be overcome. It is noted that collagen degeneration of the supraspinatus tenson and calcific depositis in the tendon may have to be dealt with later by partial acromionectomy or removal of the calcific deposits if these are advancaed in degree prior to correction of the cervical disc problem.

DESCRIPTION OF THE PREFERRED EMBODIMENTS

Figure 1:
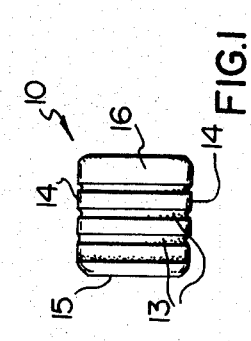
FIG. 1 is a plan view of the prosthesis according to a first embodiment of the invention.
Figure 2:
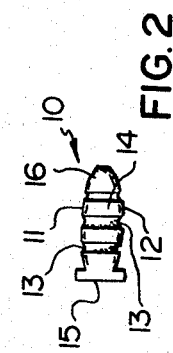
FIG. 2 is a lateral elevational view of the prosthesis of FIG. 1.
Figure 3:
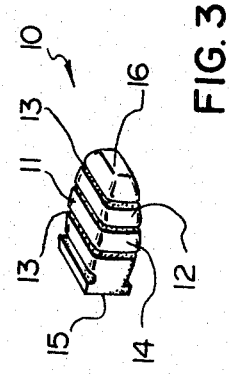
FIG. 3 is a perspective view of the prosthesis of FIGS. 1 and 2.

One embodiment of the intervertebral disc prosthesis according to the invention is shown at 10 in FIGS. 1, 2 and 3. The prosthesis 10 is formed of a thin block of biologically acceptable material having slightly convex superior and inferior surfaces 11 and 12, transverse grooves 13 in said superior and inferior surfaces and also in both lateral surfaces 14, 14, a flange or lip 15 raised from said superior and inferior surfaces at one longitudinal end of the prosthesis, and a wedge shaped tapering portion 16 at the other longitudinal end.

The prosthesis 10 is designed to replace a damaged intervertebral disc, preferably a cervical disc, in order to restore the normal intervertebral spacing. The convexity of the superior and inferior surfaces 11 and 12 corresponds closely to the slight concavities found in the inferior and superior surfaces of the vertebrae so that loading at the vertebra/prosthesis interface is spread evenly, resulting in reduced liklihood of damage to the cancellous vertebral bone structure.

The transverse grooves 13 increase the stability of the prosthesis in the disc cavity both initially and progressively with time. For initial stability the grooves create a "friction fit." It is generally only possible to insert the prosthesis when considerable traction is applied in the operating room. When the traction is released, the friction fit created by the grooves tends to resist removal of the prosthesis unless longitudinal traction is re-applied. This is believed to be because the edges of the grooves abut against bony protruberances from the vertebral surfaces.

The grooves 13 also improve the stability of the prosthesis progressively with time as fibrous and fibrocartilaginous tissue grows into conformity with the configuration of the surfaces of the prosthesis. The tissue does not grow into the structure of the prosthesis, as would be the case if the surface were porous, but rather against the surfaces to encapsulate the prosthesis. The prosthesis becomes encapsulated rapidly due to hypertrophy of the pre-vertebral fascia.

This encapsulation process has a further advantage over fibrous growth directly into the structure of the prosthesis. Removal of a prosthesis encapsulated in this way, for example if it should become infected later on, is relatively simple as the space around the prosthesis does not become vascular, as is the case with direct tissue ingrowth. After the removal of the prosthesis, the space may then be treated with a cortical cancellous bone graft to promote bony fusion as a salvage procedure.

Although transverse grooves 13 are preferred for providing the "friction-fit" because the major deforming forces tend to dislocate the prosthesis in the longitudinal (anterior-posterior) direction, other surface corrugations or projections can alternatively be employed, for example pyramidal, diamond-shape, rasp- or file-like projections are suitable. Generally any small projections, grooves or corrugations suitable to resist discloation of the prosthesis, may be employed.

The wedge-shaped tapering portion 16 allows easier insertion of the prosthesis into the disc space. The wedge shape separates the vertebrae to the required spacing as the prosthesis is tapped into place. Furthermore, the wedge shape is also better accommodated at the back of the disc space and it does not interfere with the outer edges of the vertebrae.

The flange 15 is significant in that it prevents the surgeon from inadvertently driving the prosthesis too far through the disc space, for example into the neural canal, which could result in quadriplegia. It also prevents migration of the prosthesis after termination of the operation and, in addition to the growth of fibrocartilaginous tissue into grooves 13, helps to anchor the prosthesis firmly in position.

During a severe flexion extension injury to the spine (particularly the cervical spine which is susceptible to this kind of injury) after a disc prosthesis has been implanted therein, the flange prevents the prosthesis from moving posteriorly into the neural canal as the prosthesis is carried forward with either the vertebra above or the vertebra below.

The flange also greatly facilitates gripping of the prosthesis, particularly during insertion into and removal from the disc space. The extreme difficulty of gripping a biconvex surfaced prosthesis for removal from a disc space can well be imagined since any instrument gripping the prosthesis would tend to "squirt" it further into the disc space. The disc space would have to be widened considerably to allow full insertion of the withdrawal instrument. The presence of the flange 15, however, makes removal relatively easy as it remains outside the disc space and can easily be gripped.

Despite the above advantages of the flange 15, it can be omitted if the rear edge of the prosthesis is instead provided with screw hole or the like so that the prosthesis can be attached to a holding instrument during insertion or removal. When the prosthesis is properly located the holding instrument can be removed and the screw hole filled in by means of a cover screw to prevent ingrowth of fibrous tissue. The holder can be designed to allow the prosthesis to be inserted into the disc space only to the desired depth.

As the flange 15 has advantages after the prosthesis has been inserted, it is generally preferred over the alternative suggested above.

The flange 15 is shown in the drawing projecting from both the superior and inferior surfaces 11, 12. If desired, the flange may form a projection at only one of those surfaces. Moreover, the flange need not extend laterally for the whole of the lateral width of the prosthesis, as shown, but may extend for only part of this width.

The prosthesis 10 is essentially a spacer and can be fabricated from any biologically acceptable material of suitable strength and durability, for example high density polyethylene, polymethylmethacrylate, stainless steel, or chrome cobalt alloys. The simplest material for fabrication of the prosthesis is a polymer, preferably high density polyethylene, and this may include a radioopaque marker so that the position of the prosthesis can be confirmed radiologically. Elastomeric materials are less preferred because some such materials hve been known to disintegrate in the body. Furthermore, it is generally preferable to select a material that resists compression or flexing, particularly in the case of a cervical prosthesis. It is advantageous in the cervical spine that lateral movement of the neck, as occurs when tilting the head toward either shoulder, should purposely be restricted by the design feature of the prosthesis. It is important to restrict this lateral movement at the diseased level for the following reasons:

(a) In restoring the width of the disc space, the superior inferior diameter or height of the outlet foramen is increased by the disc prosthesis;

(b) in diseased segments, the lateral or anterior posterior diameter of the canal is narrowed already by the osteophytes which form in the outlet foramen at the joints of Luschka. These osteophytes are not removed at surgery as removal of these would require much more extensive and dangerous exposure with potential problems of hemorrhage due to the proximity of the vertebral arteries.

(c) relief of the vertebral artery symptoms is obtained by restoring the artery to its normal length by introduction of the disc prosthesis.

(d) relief of the nerve root compressions symptoms is achieved by gaining some increase in the overall dimension of the foramen by the gain in height or superior inferior diameter.

(e) hence lateral bending allowed at the space would lose this advantage gained by restoration of the superior inferior diameter height of the foramen by the prosthesis with subsequent recurrence of symptoms of nerve root compression due to the continuing presence of osteophytes which take some of the available space in the foramen. The continuing presence of the osteophytes in the outlet foramen does not cause any symptoms as long as the overall dimension of the canal is adequate to allow the passage of the nerve roots without any root compression. Hence it is important that the prosthesis does not allow lateral movement at the diseased levels since this movement allows a loss of the height of the outlet foramen and hence loss of the advantage gained by introduction of the disc prosthesis;

(f) the only movement which would be advantageous in design modifications of this prosthesis, as described later, are the flexion extension movements at this space. This can be accomplished simply by a transverse cleavage plane and a simple hinge using two components of dissimilar materials such as stainless steel and high density polyethylene. This design allows flexion and extension movements at this space.

It is not essential to make both the superior and inferior surfaces of the prosthesis convex. In particular, the superior surfaces of many vertebrae are almost planar, so the inferior surface of the prosthesis 10 may similarly be planar.

The required size of the prosthesis correlates directly with the height of the patient. Hence, a small size prosthesis is used for patients up to about 5'4" in height. For the patients up to 6' a medium sized prosthesis is used and in patients taller than that a large size is required. As the size increases, each of the dimensions of the prosthesis increase slightly in size.

One length is not suitable for all people. The distance between the front of the vertebra and to the neural canal is less in a small person (below five feet) than a larger person (above six feet).

It can be generally stated that a small person has a narrower disc than a large person. Similarly the length of the prosthesis (distance from anterior part of the vertebral body to neural canal) also increased in the larger person as compared to the smaller person. The distance between the lateral surfaces also increases as the size or height of the patient increases. Hence, in putting a small size prosthesis into a very large person the thickness of the prosthesis would be inadequate to distract the space sufficiently. The total surface area would also be inadequate to distribute the weight bearing to the maximum bony surface and the depth or length would also be inadequate to provide total support for the vertebra. Similarly, in attempting to place the large size prosthesis into the small person, the vertebral body could be crushed as the oversize prosthesis is driven into a small or narrowed disc space which cannot accommodate the larger structure. This leads to wedging of the verbebrae as is seen in a compression wedge fracture. In addition, the oversize prosthesis if driven into the flange would be driven slightly into the neural canal with subsequent cord damage.

The increased thickness of using the grossly oversized prosthesis in a small person would also lead to instability of the prosthesis since the disc space would be forced into extension (in the neck) and the prosthesis would hence be sitting as a wedge which would tend to cause it to dislocate anteriorly as it would tend to be "squirted out" anteriorly.

In summary, one length is not suitable for all people. The proper length is equal to the distance from the front of the vertebra to the limit of the prepared space once the disc has been removed. It is also evident that if the osteophytes on the anterior aspect of the body, formed as a natural consequence of the disease, are removed at surgery the prosthesis can be inserted further before the flange contacts the front of the bodies.

In some cases it may be appropriate to use a depth gauge to determine the exact distance to obtain the accurate length of the prosthesis. Generally, however, the prosthesis can be standardized according to sizes used in patients of varying heights.

Figure 4:
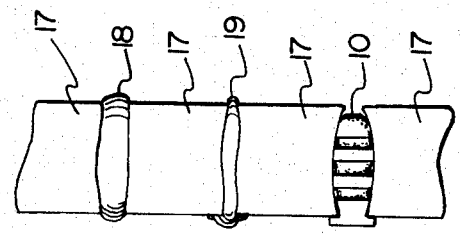
FIG. 4 is a simplified lateral representation of part of the spinal column showing natural discs and the prosthesis of FIGS. 1 to 3.

FIG. 4 is a simplified lateral representation of part of a spinal column in which vertebrae 17 are spaced by a normal disc 18, a narrowed disc 19 caused by damage, disease or degeneration, and a prosthesis 10 according to this invention. This shows how the prosthesis 10 can be used to restore the normal intervertebral disc spacing.

The prosthesis shown in FIGS. 1 to 4 is intended primarily as a cervical disc prosthesis. When a prosthesis for the lumbar area is required, it has been found advantageous to make the prosthesis in two halves, the division being in a longitudinal (posterior-anterior), vertical plane. Together, the two halves have a width equal to the total size of the space created when bilateral lumbar discectomy is carried out. Apart from the two-part structure of the lumbar prosthesis, and a difference in overall dimensions, it is the same as the cervical prosthesis described in connection with FIGS. 1 to 4.

Different surgical techniques are required for cervical prosthesis implanation and lumbar prosthesis implanation. These techniques are described in detail below.

SURGICAL TECHNIQUES

1. Cervical Disc Replacement

The patient is prepared on the operating room table under general anaesthetic and endotracheal intubation with cervical halter traction.

A sandbag or folded towel is placed between the shoulders and a small doughnut is placed under the head posteriorly to provide a certain degree of neck extension and elongation for easier exposure during surgery. The neck is prepped and square drapped anteriorly. A right-sided anterior transverse cervical incision is made approximately two or three finger breadths above the sternal notch. The level of the incision depends on the level of the cervical disc or discs involved. The incision is placed higher if the disc lesions are located high in the neck.

The platysma muscle is divided. The sternocleidomastoid and the carotid bundle are identified and retracted laterally. The strap muscles, trachea and esophagus are retracted medially. The bulging discs are identified visually and by palpation. A needle marker is placed in position and a lateral X-ray is taken in the operating room to confirm the level of the needle and consequently the level of involved discs. Straps are placed on the patient's wrists for traction while the X-ray films are taken since this allows better visualization of the C6–7 level.

Once the level of the diseased discs are determined pre-operatively have been positively identified in the operating room, the diseased discs are excised anteriorly and the space is thoroughly curetted out, removing the whole of the disc. The posterior longitudinal ligament is not removed and the neural canal is not visualized during the procedure. The periosteal elevator is then placed in the disc space and rotated to distract the spaces and restore the width of the vertebral disc space to normal. A click is heard when the space is opened up and the vertebrae are separated. The significance of this noise is that the adhesions between the two sides of the outlet foramen and the facets as well as the posterior aspect of the vertebral body is released. The height of the outlet foramen has hence been restored in the superior-inferior plane at this moment.

Once the space has been well curetted out to the posterior aspects of the body and while traction is being applied to the neck by the anaesthetist, the intervertebral disc prosthesis 10 is tapped into position. It is quite stable once in position and once the traction is released it is firmly gripped between the adjacent vertebral bodies. A lateral X-ray can be taken in the operating room at this time to confirm the restoration of the disc space width.

It is recommended that all narrowed discs visualized in the X-ray films are replaced at the time of surgery and from one to four levels can be done at any one time. The wound is subsequently closed in layers and absorbable suture material used in the skin. A light dressing is applied. A cervical collar is not essential since the prosthesis is inherently stable at the time of insertion. The average hospital stay is approximately three days and there is no particular mobilization of the neck necessary post-operatively. It is noted that the headaches, neck pain and arm pains from the cervical disc syndrome usually subside on the day of surgery. The dizziness, blackouts, and intermittent blurred vision and tinnitus related to the vertebral artery syndrome usually also disappears on the day of surgery. There is, however, some posterior cervical discomfort lasting up to one month related to stretching out of contracted ligaments.

2. Lumbar Disc Replacement

Replacement of the lumbar disc must be done through a posterior approach. This allows the surgeon to decompress any nerve roots or portion of the neural canal which are stenosed as part of the procedure. It also allows excision of any free disc fragments in the neural canal. Replacement of the lumbar disc through an anterior approach or retroperitoneal approach is impractical since the surgeon is unable to visualize or decompress the nerve roots or neural canal from an anterior approach. In addition, anterior approach is associated with increasing morbidity including problems such as impotence in the male due to stripping of fibers of the autonomic nervous system lying anteriorly.

Disc prosthesis must be inserted into the remaining space available after routine discectomy by the surgeon. Discectomy should ideally be done by bilaterally excising the whole of the posterior annulus and easily removable nucleus pulposus.

As mentioned above, a disc prosthesis may be designed specifically for the lumbar area. This prosthesis consists of two halves which together comprise a diameter equal to the total size of the space created when bilateral lumbar discectomy is done. One component is inserted from each side by retracting the cauda equina and exiting nerve root towards the opposite side to the midline while excision of the disc and disc replacement is carried out.

Figure 5:
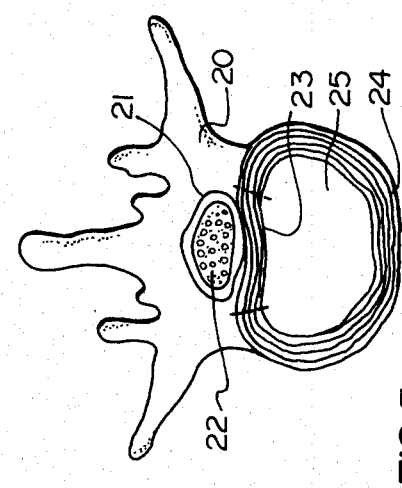

The steps of this surgical technique are shown in FIGS. 5 to 11. FIG. 5 is a schematic plan view of an intervertebral disc space above a lumbar vertebra 20 showing the neural canal 21 containing the cauda equina 22, the posterior annulus 23, the anterior annulus 24 and the nucleus pulposus 25 of the natural disc.

As shown in FIG. 6, the cauda equina 22 is moved by the surgeon to one side by a nerve root retractor 26, the posterior annulus 23 is excised to the midline and the nucleus pulposus 25 removed.

Figure 7:
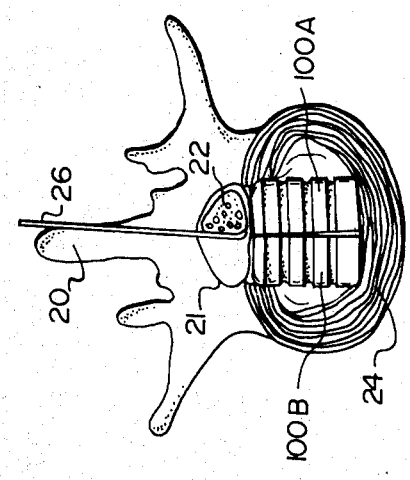
Figure 9:
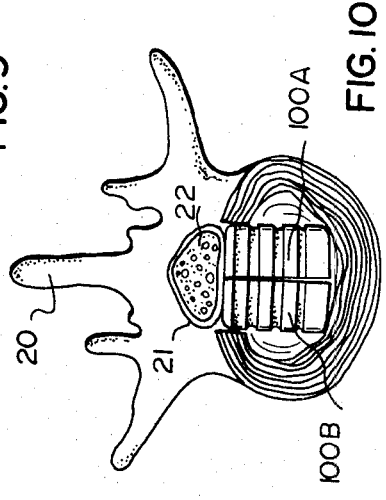
Figure 8:
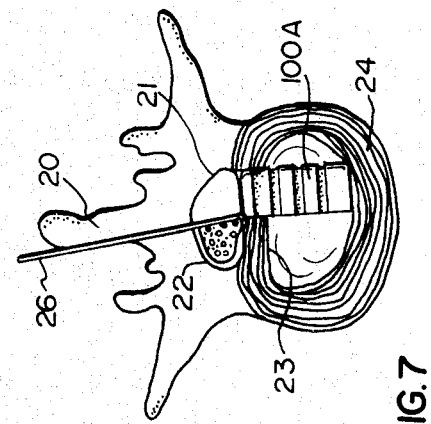
Figure 10:
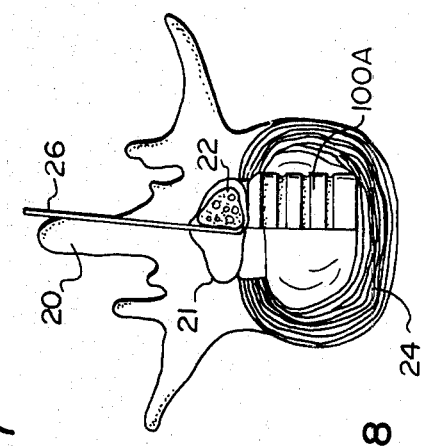

A first lumbar disc prosthesis part 100A is then inserted (as shown in FIG. 7) and then the procedure is repeated on the other lateral side (as shown in FIGS. 8 and 9) in order to insert a second lumbar disc prosthesis part 100B. The cauda equina is then released as shown in FIG. 10 and the wound closed in the usual way.

FIG. 11 is a lateral view of the implanted prostheses, the prosthesis part 100B only being visible. This view clearly shows that the anterior annulus 24 remains unaffected.

The prosthesis parts 100A and 100B act together in the same way as the cervical disc prosthesis 10. Each has a superior surface 101, an inferior surface 102, transverse grooves 103, a raised flange 105 and a wedge-shaped tapering portion 106. The lateral width of each prosthesis 100A and 100B is such that together they occupy the majority of the cavity previously occupied by the nucleus pulposus 25.

The superior and inferior surfaces 101 and 102 are designed to produce a friction fit caused by transverse grooves 103 once a laminar spreader has been removed and the overly distracted space is allowed to return to normal width. The friction fit can be provided by other surface features as in the previous embodiment. The flanges 105 are designed to prevent the prosthesis parts 100A and 100B from migrating forward towards the abdomen. They also allow ease of removal as well as ease of insertion of the prostheses. In the event of disc space infection, the flanges 105 allow ready removal of the prosthesis parts. The tapered ends 106 are designed for easy starting when the prosthesis parts are tapped into position. The biconvex shape of the natural disc space allows a natural element of stability to the prosthesis especially when the friction fit surfaces are incorporated into the design. As stated above, the prosthesis parts are preferably constructed of a rigid material e.g. high density polyethylene.

In the description above, it is noted that the recommendation is that the laminectomy should be done bilaterally and both sides or components should be inserted. However, this prosthesis also has application for the surgeon who wishes to do a hemi-laminectomy, removing the sequestrated fragment alone without approaching the opposite side since it would still act to prevent many of the problems presently seen in disc surgery. However in using the two halves of the prosthesis as recommended it is noted that the total loading or weight bearing area is doubled and this is more satisfactory and less likely to result in any problem related to erosion of prosthesis into the vertebral end plates due to uneven load distribution.

The advantages of lumbar disc replacement using a prosthesis according to the invention are as follows:

(1) Subluxation of the apophyseal joint surface facettes secondary to narrowing of the space does not occur with the disc prosthesis in position.

(2) Progressive posterior buckling of residual posterior annulus fibrosis does not occur since it has been excised as part of the surgical preparation of the space for the prosthesis.

(3) Progressive anterior buckling of the ligamentum flavum of the neural canal from behind does not occur as this is also excised in the surgical approach.

(4) Progressive deformity of the bony canal due to increasing swayback or increasing lumbar lordosis does not occur as the height of the posterior part of the disc is maintained.

(5) Progressive contact between spinous processes does not occur as this has been excised during the surgical approach. In addition, if the space cannot narrow then the spinous processes will not contact at a later date.

(6) Progressive herniation of any residual nucleus pulposus fragments, pieces of hyaline cartilage and plates, or anterior rings of the annulus fibrosis does not occur as the prosthetic disc acts as a "plug" preventing posterior migration of these tissues through the defect created surgically in the posterior annulus.

(7) Operative time involved in meticulous cleaning out and curetting out of the disc material is decreased as it is impossible for this tissue to migrate posteriorly at a later date with the prosthetic disc plug in position.

(8) The danger of fatal hemorrhage from perforating the anterior annulus with subsequent damage to the iliac vessels or veins lying anteriorly is non-existent since the surgeon no longer has to meticulously reach into the depths of the disc in an attempt to clean out all fragments which may possibly herniate at a later date. Since the prosthesis acts as a plug it would not allow posterior migration of these fragments. Since these fragments are soft in nature if they are pushed forwards towards the abdomen by the prosthesis no damage could possibly occur to the vessels.

An alternative embodiment of the disc prosthesis according to this invention is shown at 200 in FIG. 12, which is a simplified schematic cross-section of the prosthesis in position between two vertebrae 207, 207.

The prosthesis 200 is similar to the prosthesis 10 described above except that it is formed of two components 200A and 200B to allow flexion and extension movements within the structure of the prosthesis. As shown, the superior component 200A has a hemispherical projection 208 at the centre of its inferior surface 209, and the inferior component 200B has a hemispherical depression 210 at the centre of its superior surface 211. The projection 208 and depression 210 interengage to form a simple pivot allowing flexion of the prosthesis 200. Moreover, in extension of the spinal column, the two components 200A and 200B may separate by a small extent as the projection 208 may simply be withdrawn from the depression 210. Thus, extension is possible without disturbing the vertebra/prosthesis junctions and hence the fibrocartilaginous encapsulation which takes place at these junctions.

Apart from the two component structure, the prosthesis is similar to prosthesis 10 in that it has transverse grooves 203 in the superior surface 201 and the inferior surface 202, and raised flanges 205, 205 at the posterior end. Moreover, the anterior end of the prosthesis can be formed into a tapering wedge-shaped portion by pivoting the components 200A, 200B so that their anterior ends approach each other.

Advantageously, one of the components is made of stainless steel and the other component is made of high density polyethylene. These dissimilar materials provide a low co-efficient of friction at the pivot.

The prosthesis 200 can be used as a cervical prosthesis or as one half of a lumbar prosthesis as described above in connection with prosthesis parts 100A, 100B.

FIG. 13 is a simplified lateral view of the prosthesis 200 used as a cervical disc prosthesis located between two cervical vertebrae 214,214, and FIG. 14 is a similar view of the prosthesis 200 used as a lumbar disc prosthesis located between lumbar vertebrae 215,215.

Although the embodiment shown in the drawings has the projection 208 in superior component 200A and the depression 210 in the inferior component 200B, this arrangement can clearly be reversed. Moreover, alternative forms of pivotal joint between components 200A and 200B can be employed.

FIG. 15 is a cross-sectional view of a prosthesis having alternative holding means rather than the flange 15 of FIG. 1. The prosthesis 300 has a circular cross-section hole 301 in the posterior end. The hole is threaded to secure the threaded end 302 of an elongated holding instrument 303. After implantation of the prosthesis, the holding instrument 303 is unscrewed and withdrawn. If necessary, the hole 301 can be plugged with a removable plug (not shown).

Although the prosthesis has been described in connection with the cervical spine and lumbar spine, it can also be used in the dorsal spine for the correction of dorsal spondylitis with radicuilitis.

The prosthesis according to any embodiment of the invention can be made available to surgeons as part of a kit including the necessary surgical instruments and templates for ascertaining the correct size of prosthesis. The instrumentation may be held in an instrument case designed for cervical or lumbar disc surgery.

It is believed that persons skilled in this art will readily perceive various effective modifications and variations in the embodiments described above. Such modifications and variations are included within the scope of this invention as defined by the following claims.

I claim:

1. An intervertebral disc prosthesis, comprising a body of substantially rigid, non-porous, biologically compatible material having a superior surface, an inferior surface, opposed lateral surfaces and opposed anterior and posterior ends, each of said superior surface and inferior surface being substantially flat in the lateral-lateral direction over the entirety of said surfaces and, in the anterior-posterior direction, corresponding generally with the shape of a vertebral surface adjacent a disc space, and means located at one of said opposed anterior and posterior ends for facilitating holding of the prosthesis during its insertion into said disc space.

2. A prosthesis according to claim 1 wherein at least one of said superior and inferior surfaces is substantially flat in the anterior-posterior direction.

3. A prosthesis according to claim 1 wherein at least one of said superior and inferior surfaces is slightly convex in the anterior-posterior direction.

4. A prosthesis according to claim 1 wherein both of said anterior and posterior surfaces are slightly convex in the anterior-posterior direction.

5. A prosthesis according to claim 1 wherein said holding means comprises a raised flange on said body at said one end projecting from at least one of said superior and inferior surfaces at said end.

6. A prosthesis according to claim 1 wherein said holding means comprises a hole extending into said body at one of said opposed ends for receiving a holding instrument.

7. A prosthesis according to claim 6 wherein means are provided within said hole for detachably securing said instrument.

8. A prosthesis according to claim 7 wherein said means for detachably securing said instrument comprises a screw thread intended to engage a corresponding thread provided on the holding instrument.

9. A prosthesis according to claim 1 wherein at least one of said superior and inferior surfaces has surface characteristics for increasing friction between said surface and said adjacent vertebral surface when the prosthesis is implanted within the disc space.

10. A prosthesis according to claim 9 wherein said surface characteristics are grooves generally parallel to said anterior and posterior ends.

11. A prosthesis according to claim 9 wherein said surface characteristics are small projections from said surface.

12. A prosthesis according to claim 9 wherein said surface characteristics are shallow corrugations on said surface.

13. A prosthesis according to claim 1 wherein the other of said anterior and posterior ends is wedge-shaped to facilitate insertion of the prosthesis into the disc space.

14. A prosthesis according to claim 1 wherein said body is made of two components separated from each other along a superior-inferior plane extending between said opposed anterior and posterior ends.

15. A prosthesis according to claim 1 wherein said body is made of two components, one of said components defining the superior surface and the other of said components defining said inferior surface, the components being mutually pivotally connected to permit limited variations of the orientation of said superior and inferior surfaces with respect to each other in the anterior-posterior direction.

16. A prosthesis according to claim 15 wherein said pivotal connection of the components is provided by a projection from one of said components engageable with a depression in the other of said components.

17. A prosthesis according to claim 15 wherein one of said components is made of metal and the other is made of a rigid polymer.

18. A prosthesis according to claim 1 wherein said substantially rigid biologically compatible material is selected from the group consisting of high density polyethylene, polymethylmethacrylate, stainless steel and chrome cobalt alloys.

19. A prosthesis according to claim 1 wherein said substantially rigid biologically compatible material is polymethylmethacrylate.

20. A prosthesis according to claim 1 wherein said substantially rigid biologically compatible material is polyethylene.

21. An intervertebral disc prosthesis, comprising a body of substantially rigid, non-porous, biologically compatible material having a superior surface, an inferior surface, opposed lateral surfaces and opposed anterior and posterior ends, each of said superior and inferior surfaces being substantially flat in the lateral-lateral direction over the entirety of said surfaces and, in the anterior-posterior direction, corresponding generally with the shape of a vertebral surface adjacent a disc space, and a flange provided on said body at one of said opposed ends projecting beyond at least one of said inferior and superior surfaces at said end to facilitate holding of the prosthesis during its insertion into the disc space and to form an abutment to limit the depth of said insertion.

22. A prosthesis according to claim 20 wherein at least one of said superior and inferior surfaces is substantially flat in the anterior-posterior direction.

23. A prosthesis according to claim 21 wherein at least one of said superior and inferior surfaces is slightly convex in the anterior-posterior direction.

24. A prosthesis according to claim 21 wherein both of said anterior and posterior surfaces are slightly convex in the anterior-posterior direction.

25. A prosthesis according to claim 21 wherein at least one of said superior and inferior surfaces has surface characteristics for increasing friction between said surface and said adjacent vertebral surface when the prosthesis is implanted within the disc space.

26. A prosthesis according to claim 25 wherein said surface characteristics are grooves generally parallel to said anterior and posterior ends.

27. A prosthesis according to claim 25 wherein said surface characteristics are small projections from said surface.

28. A prosthesis according to claim 25 wherein said surface characteristics are shallow corrugations on said surface.

29. A prosthesis according to claim 21 wherein the other of said anterior and posterior ends is wedge-shaped to facilitate insertion of the prosthesis into the disc space.

30. A prosthesis according to claim 21 wherein said body is made of two components separated from each other along a superior-inferior plane extending between said opposed anterior and posterior ends.

31. A prosthesis according to claim 21 wherein said body is made of two components, one of said components defining the superior surface and the other of said components defining said inferior surface, the components being mutually pivotally connected to permit limited variations of the orientation of said superior and inferior surfaces with respect to each other in the anterior-posterior direction.

32. A prosthesis according to claim 21 wherein said substantially rigid biologically compatible material is selected from the group consisting of high density polyethylene, polymethylmethacrylate, stainless steel and chrome cobalt alloys.

33. A prosthesis according to claim 21 wherein said substantially rigid biologically compatible material is polymethylmethacrylate.

34. A prosthesis according to claim 21 wherein said substantially rigid biologically compatible material is polyethylene.

35. An intervertebral disc prosthesis, comprising a body of substantially rigid, non-porous, biologically compatible material having a superior surface, an inferior surface, opposed lateral surfaces and opposed anterior and posterior ends, each of said superior and inferior surfaces being substantially flat in the lateral-lateral direction over the entirety of said surfaces and, in the anterior-posterior direction, corresponding generally with the shape of a vertebral surface adjacent a disc space, said body being made of two components separated from each other along a superior-inferior plane extending between said opposed anterior and posterior ends.

36. A prosthesis according to claim 35 wherein at least one of said superior and inferior surfaces is substantially flat in the anterior-posterior direction.

37. A prosthesis according to claim 35 wherein at least one of said superior and inferior surfaces is slightly convex in the anterior-posterior direction.

38. A prosthesis according to claim 35 wherein both of said anterior and posterior surfaces are slightly convex in the anterior-posterior direction.

39. A prosthesis according to claim 35 wherein at least one of said superior and inferior surfaces has surface characteristics for increasing friction between said surface and said adjacent vertebral surface when the prosthesis is implanted within the disc space.

40. A prosthesis according to claim 39 wherein said surface characteristics are grooves generally parallel to said anterior and posterior ends.

41. A prosthesis according to claim 39 wherein said surface characteristics are small projections from said surface.

42. A prosthesis according to claim 39 wherein said surface characteristics are shallow corrugations on said surface.

43. A prosthesis according to claim 35 wherein one of said anterior and posterior ends is wedge-shaped to facilitate insertion of the prosthesis into the disc space.

44. A prosthesis according to claim 35 wherein each of said components has means located at one of said opposed anterior and posterior ends for facilitating holding of the component during its insertion into said disc space.

45. A prosthesis according to claim 44 wherein said holding means comprises a raised flange on said body at said one end projecting from at least one of said superior and inferior surfaces at said end.

46. A prosthesis according to claim 44 wherein said holding means comprises a hole extending into said body at one of said opposed ends for receiving a holding instrument.

47. A prosthesis according to claim 46 wherein means are provided within said hole for detachably securing said instrument.

48. A prosthesis according to claim 47 wherein said means for detachably securing said instrument comprises a screw thread intended to engage a corresponding thread provided on the holding instrument.

49. A method of implanting an intervertebral disc prosthesis in the cervical region of the spine, wherein said prosthesis comprises a body of biologically compatible material having a superior surface, an inferior surface and opposed anterior and posterior ends, means located at one of said opposed ends for facilitating holding of the prosthesis during its insertion into and removal from an intevertebral disc space, and means for increasing friction between said surfaces and adjacent vertebrae when the prosthesis is implanted within an intervertebral disc space, said means for facilitating holding of the prosthesis comprising a hole extending into said body at one of said opposed ends for receiving a holding instrument, and means within said hole for detachably securing said instrument, said method comprising:

(a) exposing the affected region of the spine anteriorly;
(b) curretting out the affected disc or discs without visualizing the neural canal;
(c) attaching the prosthesis to a holding instrument by inserting said instrument into said hole extending into the body of the prosthesis;
(d) inserting the prosthesis into the disc space with the aid of said holding instrument;
(e) detaching said holding instrument from said prosthesis;
(f) closing the wound.

50. A method of implanting an intervertebral disc prosthesis in the lumbar region of the spine, said prosthesis being in the form of two parts for location in side-by-side relationship, each of said parts comprising a body of biologically compatible material having a superior surface, an inferior surface and opposed anterior and posterior ends, means located at one of said opposed ends for facilitating holding of the part during its insertion into and removal from an intevertebral disc space, and means for increasing friction between said surfaces and adjacent vertebrae when the part is implanted within an intevertebral disc space, said means for facilitating holding of the part comprising a hold extending into said body at one of said opposed ends for receiving a holding instrument, and means within said hole for detachably securing said instrument, said method comprising:

(a) exposing the affected region of the spine posteriorly;
(b) retracting the cauda equina to one side;
(c) excising the exposed posterior annulus and nucleus pulposus to the midline;
(d) attaching one part of the prosthesis to a holding instrument by inserting said instrument into the hole extending into the body of said part;
(e) inserting said part into the disc space with the aid of said holding instrument;
(f) detaching said holding instrument from said part;
(g) retracting the cauda equina to the opposite side and repeating steps (c), (d), (e) and (f) on the other side of said midline; and
(h) closing the wound.

51. A method of implanting an intervertebral disc prosthesis in the cervical region of the spine, wherein said prosthesis comprises a body of biologically compatible material having a superior surface, an inferior surface, opposed anterior and posterior ends, and opposed lateral side surfaces, and a flange provided on said body at one of said opposed ends projecting beyond at least one of said inferior and superior surfaces at said end to form an abutment to limit the depth of insertion of the body into an intervertebral disc space, said method comprising:

(a) exposing the affected region of the spine anteriorly;
(b) curretting out the affected disc or discs without visualizing the neural canal;
(c) inserting the prosthesis into the exposed disc space at the end opposite the flange and continuing insertion until the flange engages against a vertebra; and
(f) closing the wound.

52. A method of implanting an intevertebral disc prosthesis in the lumbar region of the spine, said prosthesis being in the form of two parts for location in side-by-side relationship, each of said parts comprising a body of biologically compatible material having a superior surface, an inferior surface, opposed anterior and posterior ends, and opposed lateral side surfaces, and a flange provided on said body at one of said opposed ends projecting beyond at least one of said inferior and superior surfaces at said end to form an abutment to limit the depth of insertion of the body into an intervertebral disc space, said method comprising:

(a) exposing the affected region of the spine posteriorly;
(b) retracting the cauda equina to one side;
(c) excising the exposed posterior annulus and nucleus pulposus to the midline;
(d) inserting one of said parts into the exposed disc space at the end opposite the flange and continuing insertion until the flange engages against a vertebra;
(e) retracting the cauda equina to the opposite side and repeating steps (c) and (d) on the other side of said midline; and
(f) closing the wound.

* * * * *